United States Patent
Kim et al.

(12)

(10) Patent No.: US 6,406,897 B1
(45) Date of Patent: Jun. 18, 2002

(54) MODIFIED PROTEIN, METHOD FOR PREPARATION THEREOF AND COMPOSITIONS FOR EXTERNAL APPLICATION CONTAINING THE MODIFIED PROTEIN

(75) Inventors: Mu Sung Kim; Sung Gu Lee, both of Suwon; Byung Young Kang, Seoul; Dong Chul Lee, Sungnam, all of (KR)

(73) Assignee: Pacific Corporation, Seoul (KR)

( * ) Notice: Subject to any disclaimer, the term of this patent is extended or adjusted under 35 U.S.C. 154(b) by 0 days.

(21) Appl. No.: 09/453,965

(22) Filed: Dec. 3, 1999

(30) Foreign Application Priority Data

Mar. 19, 1999 (KR) .............................................. 99-9380

(51) Int. Cl.$^7$ ........................... C12N 9/96; A61K 38/54
(52) U.S. Cl. ...................... 435/188; 435/183; 435/184; 424/94.3
(58) Field of Search ................................ 435/188, 184, 435/183; 424/94.3

(56) References Cited

U.S. PATENT DOCUMENTS

| | | | |
|---|---|---|---|
| 4,556,554 A | 12/1985 | Calvo | 424/70 |
| 5,230,891 A | 7/1993 | Nakayama et al. | 424/401 |
| 5,275,814 A | * 1/1994 | Wojdani | |

FOREIGN PATENT DOCUMENTS

| EP | 0 803 257 | 10/1997 |
|---|---|---|
| JP | 4-141097 | 5/1992 |

OTHER PUBLICATIONS

Fujimiya etal. Selective turnoricidal effect of soluble proteoglucan extracted from the basidiomycete, agaricus blazei murill, mediated via natural killer cell activation and apoptosis (May 1998) Cancer Immunology Immunotherapy, vol. 46, No. 3, p. 147–159.*

Watanabe et al. Antitumor effects of pronase–treated fragments, glycopeptides, from ovomucin in hen egg white in a double grafted tumor system (1998) J. Agric. Food Chem., vol. 46, pp. 3033–3038.*

Ebina et al., Antitumor eefct of intramoral administration of biological response modifiers: induction of immunosuppresive acidic protein, a type of alpha1–acid glycoprotein in mice (Jan. 1994) Jpn. J. Cancer Res., vol. 85, pp. 93–100.*

Masunaga et al., The Protease as a Cleansing Agent and Its Stabilization by Chemical Modification, (1993) J. SCCJ, vol. 27, No. 3, p. 276–288.

* cited by examiner

Primary Examiner—Jon P. Weber
Assistant Examiner—Harry J Guttman
(74) Attorney, Agent, or Firm—Foley & Lardner

(57) ABSTRACT

A protein modified to improve its stability, said modified protein being coupled to a β-1,3-glucan branched with β-1,6-linkage is provided. A method for the production thereof and a cosmetic or dermatological composition comprising the modified protein are also provided. The modified protein shows an improved stability while retaining its activity and being free of skin irritation.

13 Claims, No Drawings

MODIFIED PROTEIN, METHOD FOR PREPARATION THEREOF AND COMPOSITIONS FOR EXTERNAL APPLICATION CONTAINING THE MODIFIED PROTEIN

BACKGROUND OF THE INVENTION

1. Field of the Invention

The present invention is related to a protein modified to improve its stability and a method for producing the same. More particularly, the present invention is related to a protein coupled to β-1,3-glucan branched with β-1,6-linkage, which shows an improved stability while retaining its activity, to a method for the production thereof, and to a composition for external or topical application comprising the stabilized proteins.

2. Description of the Related Arts

Proteins play various roles in living body, for example as an biocatalyst in the metabolisms, as signal transmitting agents, or the like and are commonly used advantageously in a variety of applications such as laundry industry (e.g. detergents), cosmetic industry, pharmaceutical compositions (e.g. digestants, anti-inflammatory drugs and the like), food industry (e.g. meat tenderizing agents) and so on.

However, their uses have been limited due to their instability, antigenicity, or other safety problems. In fact, in addition to skin irritation, unsatisfactory effectiveness on the skin and/or difficulty in the production of the external or topical application compositions such as cosmetic or dermatological compositions incorporated with the proteins, the short shelf-life has restricted the practical use of these compositions.

Several attempts such as immobilization or chemical modification have been made to improve the stability of the proteins so far. Although these attempts did not provide a satisfactory result, representative examples thereof are explained below.

U.S. Pat. No. 4,556,554 teaches a cosmetic composition for removal of sebum exudate from the skin, which comprises immobilized enzymes in cosmetically acceptable vehicles, and the enzymes are immobilized to functional polymers in known manners by chemical and or physical means. They are released from immobilization upon application to the skin. However, this immobilization does not provide a satisfactory improvement of stability of the enzymes in the composition.

Masunaga et al (T. Masunaga et al., IFSCC, Yokohama, A205, pp 483–501) reports proteases which are chemically coupled to polyethylene glycol. The proteases show improved stability and reduced skin-irritation. But they still have drawbacks that their shelf-time is not sufficiently prolonged and their preparation is complex.

U.S. Pat. No. 5,230,891 assigned to Kanebo Limited teaches a modified protease and their production method. Polysaccharide such as dextran, alginic acids or carrageenin is reacted with cyanuric trichloride to give a triazine ring-bound polysaccharide, which is reacted with protease to give a protease coupled to polysaccharide via triazine ring. This method still has a drawback that it is very complicated.

EP 0,803,257 A2 and JP 4-141097A teach an enzyme stabilization by oxidative process using polysaccharides. Thus-stabilized enzymes can, for example, be attached to surfaces of medical devices to minimize undesirable biological reaction associated with medical devices or attached to the surface of the reactor. However, it is not certain the stabilized enzymes can be incorporated into cosmetic or dermatological compositions Therefore, there has been a need to provide proteins so stabilized so as to be incorporated into compositions for external or topical applications.

SUMMARY OF THE INVENTION

The present invention provides a modified protein, which has an improved stability, said protein being coupled to β-1,6 residue branched from β-1,3-glucan.

The present invention further provides a method for producing the modified protein, which comprises the steps of (a) reacting a glucan with periodates to oxidize β-1,6 residue of the glucan into aldehyde;

(b) removing unreacted periodates from the reaction solution;

(c) adding to the reaction solution a protein in an amount of 0.00001~10.0% by weight and allowing the protein to contact with the oxidized glucan; and (d) adding to the reaction solution a reducing agent in an amount of 0.0001~1.0% by weight.

The method may further comprise the step of washing the product obtained in the step (d).

The present invention still provides a composition for external or topical application, which comprises the modified protein as an active ingredient.

The present invention will be described in detail below.

DETAILED DESCRIPTION OF THE INVENTION

According to the present invention, the protein is stabilized by coupling to β-1,3-glucan regularly branched with β-1,6-linkage (herein after referred to simply as "glucan"). The glucan has a neutral pH in aqueous phase, has a triple helix shape contributing to its stability, and can be modified only at its β-1,6-residue by chemical means. In contrast, polysaccharides such as dextran are modified randomly or at every residue. Therefore, glucan allows a unique modification of proteins in terms of coupling index between glucan and protein, and stability and activity of the modified protein.

The glucan employed according to the invention may include schizophyllan originated from *Schizopyllum commune*, scleroglucan from Sclerotinia sp., lentinan from *Lentinus edodes*. Other glucans can be employed as long as they have β-1,3-chain branched with regular β-1,6-linkage.

The glucans as naturally occurred have usually a molecular weight ranging from several hundred thousands to several millions. They can be used as they are, or treated by mechanical or chemical means to have a molecular weight from about 50,000 to several hundred thousands. For example, microfluidizer, sonicator or β-glucanase treatment can be used to break the intact glucan to give a smaller molecular weight glucans. The term of "glucan" is used herein to include the intact glucans as well as the small molecular weight glucans.

The glucans may be used in an aqueous solution having a concentration of 0.001~20.2% by weight, and preferably 0.1~5.0% by weight.

The proteins which can be modified to improve their stability according to the present invention may include, but not limited thereto, proteases such as papain, bromelain, ficin, trypsin, chymotrypsin, collagenase, elastase, plasmin or bacterial protease; carbohydrate-lysis enzymes such as amylase, glucoamylase, cellulase, pectinase, xylanase, α-glucosidase, β-glucosidase, β-galactosidase, β-galactosidase, β-glucanase, chitinase or mannanase; lipases such as phospholipase or triacylglycerol hydrolase; nucleic acid lysis enzymes such as DNase or RNase; phosphatases; lysozymes; catalases; superoxide dismutases; transglutamninases, peroxidases; photolyases; complex enzymes originated from microorganisms; cytokines;

growth factors; hormones; antigens; antibodies; immunoglobulins; lactoferrins; metallothioneins; thioredoxins; antimicrobial proteins; or antioxidative proteins;. The proteins also include active peptides thereof or conjugates with saccharides or lipids. They may be used singly or in combinations thereof.

The method for the production of the modified proteins will be described in detail hereinafter.

The method comprises the steps of (a) reacting a glucan with periodates to oxidize β-1,6-linkage of the glucan into aldehyde; (b) removing unreacted periodates from the reaction solution; (c) adding to the reaction solution a protein in an amount of 0.00001~10.0% by weight and allowing the protein to contact with the oxidized glucan; and (d) adding to the reaction solution a reducing agent in an amount of 0.0001~1.0% by weight. The method may further comprise the step of washing the desired product obtained in the step (d).

The step (a) is to oxidize β-1,6-residue of the glucan into aldehyde, which allows a coupling between the glucan and the protein. Periodates are used in an amount of 0.1~50.0 molar equivalents, and preferably 2~5 molar equivalents with respect to one mole of glucan. The reaction mixture is allowed to react in the dark with stirring. Periodates may include, but not limited to, $HIO_4$, $H_5O_6$, $NaIO_4$, $Na_3H_2IO_4$ or $KIO_4$. After the reaction, ethylene glycol may be added to the reaction mixture to stop the excessive oxidation reaction, if necessary. The ethylene glycol may be used in an amount of 0.01~10.0% by weight.

The step (b) is to remove the unreacted periodates and may be carried out in known manners such as dialysis or ultrafiltration using a membrane having a molecular cut off of 1,00~500,000 and preferably 10,000~100,000.

The step (c) is to react the oxidized glucan in the step (a) and the protein to form Schiff's base between the aldehyde of β-1,6-residue of the glucan and amino group of the protein. The protein is used in an amount of 0.00001~10.0% by weight and preferably 0.001~5.0% by weight based on the glucan solution obtained in the step (b).

The step (d) is reduce the Schiff's base and may be carried out by adding a reducing agent in an amount of 0.001~1.0% by weight and preferably 0.01~0.1% by weight based on the Schiff's base solution in the step (c). The reducing agent may include, but not limited to, sodium borohydride($NaBH_4$), sodium cyanoborohydride ($NaBH_4$), amine borane or the like. At this step, lysine may be added in an amount of 0.01~10% by weight and preferably 0.1~1.0% by weight to the reaction mixture to neutralize the unreacted aldehyde group.

After the step (d), the modified (stabilized) protein obtained in the step (d) may be washed by known methods such as dialysis or ultrafiltration using a membrane having a molecular cut off of 1,000~500,000 and preferably 10,000~100,000 (Step (e)).

All the steps is preferably carried out under conditions which do not cause any degeneration or activity loss of the protein to be modified. Such conditions may include, but not limited to, the temperature of about 0° C. to room temperature with mild stirring.

For the present invention, the different proteins may be modified simultaneously or in turn.

The stabilized protein may be incorporated into cosmetic or dermatological compositions for topical or external application for use in corneum-removal, sebum control, anti-inflammation, skin soothing, acne control, anti-oxidation, toxin clearance, metal ion clearance, skin elasticity improvement, wrinkle removal, anti-aging, skin whitening, tanning, depilatory prevention and inhibition, hair-removal, anti-bacterial or anti-fungal action, deodorization, sun-burn repair, wound healing and the like. The amount of the stabilized protein to be incorporated in the composition may be decided by the ordinary skilled in the art and may be in a range from 0.00001 to 100% by weight. Thus, the compositions for external or topical application according to the present invention comprises 0.00001 to 100% by weight of the stabilized protein and cosmetically or dermatologically acceptable vehicles. These vehicles are well known to the skilled in the art and may be chosen depending on the kind, formulation and usage of the composition.

The composition may have a cosmetic formulation such as cleansing lotion, cleansing cream, skin milk, emollient lotion, massage cream, emollient cream, make-up base, lipstick, facial pack, facial gel, shampoos, rinses, hair-tonics, or soaps, or dermatological composition such as lotions, ointments, gels, creams, patches or sprays.

The present invention will be described by way of various preparation and experimental examples, but should not be interpreted to be limited to these examples.

PREPARATION EXAMPLE 1

To 50 ml of 0.5wt % aqueous solution of schizophyllan (MW 2,000,000), 2 g of sodium peroxide ($NaIO_4$) was added, and the resulting mixture was allowed to stand in the dark at 4° C. for 1 hour with stirring. The resulting schizophyllan solution was subjected to dialysis over membrane (MW cut off 10,000) in the dark at 4° C. for 48 hours. The dialysis was carried out with replacement of 2500 ml water for every 12 hours.

When the volume of the schizophyllan solution was increased to about 100 ml, 0.1 wt % of papain was added and the resulting solution was stirred for 2 hours in the dark at 4° C.

Sodium borohydride (0.05 g) was added to the schizophyllan-papain solution followed by stirring for 4 hours. Lysine (0.1 g) was added and the resulting mixture was stirred for 2 hours in the dark at 4° C.

The resulting schizophyllan-papain solution was subjected to the dialysis as described in the above to obtain a solution of papain coupled to schizophyllan ("GE-1"). The yield of the GE-1 was 95% based on the enzyme activity.

PREPARATION EXAMPLE 2

To 50 ml of 1 wt % aqueous solution of scleroglycan, which was treated with microfluidizer to have MW 300,000, 2 g of potassium peroxide ($KIO_4$) was added, and the resulting mixture was allowed to stand in the dark at 4° C. for 1 hour with stirring. The resulting scleroglucan solution was subjected to ultrafiltration on a membrane (MW cut off 30,000) in the dark at room temperature using 10,000 ml of water.

To thus obtained scleroglucan solution (about 50 ml), 0.5 wt % of lysozyme was added and the resulting solution was stirred for 1 hour in the dark at 4° C.

Sodium borohydride (0.05 g) was added to the scleroglucan-lysozyme solution followed by stirring for 2 hours in the dark at 4° C.

The resulting scleroglucan-lysozyme solution was subjected to the ultrafiltration as described in the above to obtain a solution of lysozyme coupled to scleroglucan ("GE-2"). The yield of the GE-2 was 93% based on the enzyme activity.

PREPARATION EXAMPLE 3

To 50 ml of 0.5 wt % aqueous solution of schizophyllan (MW 1,000,000), 2 g of sodium peroxide (NaIO$_4$) was added, and the resulting mixture was allowed to stand at room temperature for 1 hour with stirring. The resulting schizophyllan solution was subjected to dialysis over membrane (MW cut off 10,000) in the dark at 4° C. for 48 hours. The dialysis was carried out with replacement of 2500 ml water for every 12 hours.

When the volume of the schizophyllan solution was increased to about 100 m, 0.1 g of papain was added and the resulting solution was stirred for 2 hours at room temperature.

Sodium borohydride (0.1 g) was added to the schizophyllan-papain solution followed by stirring at room temperature for 10 minutes. And, 0.1 wt % of lysozyme (0.1 g) was added to the reaction mixture, and the resulting mixture was allowed to react for 2 hours. Sodium borohydride (0.04 g) and lysine (0.1 g) were added and the resulting mixture was stirred for 24 hours.

The resulting mixed solution of schizophyllan-papain and schizophyllan-lysozyme was subjected to the dialysis as described in the above to obtain a solution of papain and lysozyme, which were coupled to schizophyllan ("GE-3"). The yield of the GE-1 was 95% based on the enzyme activity.

PREPARATION EXAMPLE 4

To 5 ml of 0.1 wt % aqueous solution of schyzophyllan (MW 2,000,000), 0.05 g of sodium peroxide (NaIO$_4$) was added, and the resulting mixture was allowed to stand in the dark at 4° C. for 1 hour with stirring. The resulting schyzophyllan solution was subjected to dialysis over membrane (MW cut off 1,000) in the dark at 4° C. for 48 hours. The dialysis was carried out with replacement of 2500 ml water for every 12 hours.

To thus obtained schizophyllan solution, 0.01 wt % of human recombinant epidermal growth factor ("hrEGF") (Sigma-Aldrich Co.) was added and the resulting solution was stirred for 2 hours in the dark at 4° C.

Sodium borohydride (0.002 g) was added to the schizophyllan-hrEGF solution followed by stirring for 4 hours. The resulting schizophyllan-hrFGF solution was subjected to the dialysis as described in the above to obtain a solution of hrEGF coupled to schizophyllan ("glucan-hrEGF conjugate").

Comparative Preparation Example 1

To 50 ml of 1 wt % aqueous solution of dextran (MW 500,000), 2 g of sodium peroxide (NaIO$_4$) was added, and the resulting mixture was allowed to stand in the dark at 4° C. for 1 hour with stirring. The resulting dextran solution was subjected to dialysis over membrane (MW cut off 10,000) in the dark at 4° C. for 48 hours. The dialysis was carried out with replacement of 2500 ml water for every 12 hours.

When the volume of the dextran solution was increased to about 100 ml, 0.1 wt % of papain was added and the resulting solution was stirred for 2 hours in the dark at 4° C.

Sodium borohydride (0.05 g) was added to the dextran-papain solution followed by stirring for 4 hours. Lysine (0.1 g) was added and the resulting mixture was stirred for 2 hours in the dark at 4° C.

The resulting glucan-papain solution was subjected to the dialysis as described in the above to obtain a solution of papain coupled to glucan. The yield of the desired product was 65% based on the enzyme activity.

Comparative Preparation Example 2

By following the procedure in Comparative Preparation Example 1 except using lysozyme instead of papain, lysozyme coupled to dextran was obtained. The yield of the desired product was 61 % based on the enzyme activity.

Experimental Example 1

GE-1 or GE-3 in Preparation Examples 1 or 3, respectively, native papain or modified papain in Comparative Preparation Example 1 was evaluated for its activity with regard to the lapse of time. The protease activity was measured according to the method of Erlanger et al. (K. E. Erlanger et al., Arch. Biochem. Biophys., 95, pp271~278, 1961). The results are shown in Table 1.

TABLE 1

|  | Prep. Ex. 1 (GE-1) | | Prep. Ex. 3 (GE-3) | | Native Papain (0.1%) | | Comp. Prep. Ex. 1 (0.1%) | |
| --- | --- | --- | --- | --- | --- | --- | --- | --- |
|  | 30° C. | 45° C. | 30° C. | 45° C. | 30° C. | 45° C. | 30° C. | 45° C. |
| Day 0 | 100 | 100 | 100 | 100 | 100 | 100 | 100 | 100 |
| Day 10 | 100 | 100 | 100 | 100 | 18 | 10 | 65 | 40 |
| Day 30 | 100 | 100 | 100 | 100 | 4 | 0 | 20 | 10 |
| Day 60 | 100 | 98 | 100 | 98 | 0 | 0 | 15 | 10 |
| Day 90 | 100 | 95 | 100 | 95 | 0 | 0 | 14 | 9 |

As can be seen from Table 1, the papain modified according to the present invention showed an improved stability when compared with the native papain or the papain modified by the conventional method.

Experimental Example 2

GE-2 or GE-3 in Preparation Examples 2 or 3, respectively, native lysozyme or modified lysozyme in Com parative Preparation Example 2 was evaluated for its activity with regard to the lapse of time. The lysozyme activity was measured according to the method of Shugar (D. Shugar, Biochem. Biophys. Acta., 8, p302, 1952). The results are shown in Table 2.

TABLE 2

|  | Prep. Ex. 2 (GE-2) | | Prep. Ex. 3 (GE-3) | | Native Lysozyme (0.1%) | | Comp. Prep. Ex. 1 (0.1%) | |
| --- | --- | --- | --- | --- | --- | --- | --- | --- |
|  | 30° C. | 45° C. | 30° C. | 45° C. | 30° C. | 45° C. | 30° C. | 45° C. |
| Day 0 | 100 | 100 | 100 | 100 | 100 | 100 | 100 | 100 |
| Day 10 | 100 | 100 | 100 | 100 | 25 | 10 | 60 | 45 |
| Day 30 | 100 | 100 | 100 | 100 | 9 | 5 | 22 | 12 |
| Day 60 | 100 | 100 | 100 | 98 | 0 | 0 | 14 | 10 |
| Day 90 | 100 | 100 | 100 | 96 | 0 | 0 | 14 | 8 |

As can be seen from Table 2, the lysozyme modified according to the present invention showed an improved stability when compared with the native lysozyme or the lysozyme modified by the conventional method.

Experimental Example 3

GE-1 or GE-3 in Preparation Examples 1 or 3, respectively, native lysozyme or modified lysozyme in Comparative Preparation Example 2 was evaluated for its action on the corneum, an insoluble substrate for papain.

Thus, corneum was taken from lower legs of healthy volunteers using D-squame and placed on discs. The discs were placed in a enzyme solution, which had been adjusted to have a certain value of activity, and allowed to react for 37° C. At an interval of 12 hours, the discs were removed from the enzyme solution and measured for the disintegration of the corneum thereon. The disintegration of corneum was measured by immersing the disc into 0.2% Nile blue A solution for 10 minutes, rinsing the disc with distilled water and determining the disintegration using chromameter. The results are shown in Table 3.

TABLE 3

(Unit: % Disintegration)

|  | Prep. Ex. 1 (GE-1) | Prep. Ex. 2 (GE-3) | Native Papain | Comp. Prep. Ex. 1 |
| --- | --- | --- | --- | --- |
| Hour 0 | 0 | 0 | 0 | 0 |
| Hour 12 | 20 | 12 | 20 | 5 |
| Hour 24 | 55 | 43 | 48 | 20 |
| Hour 36 | 100 | 90 | 90 | 55 |
| Hour 42 | 100 | 100 | 92 | 64 |

As can be seen from Table 3, the papain modified according to the present invention showed the similar activity to that of native papain while retaining its activity for a longer time, i.e. showed a greater stability than the native papain. Moreover, it could be affirmed that the papain modified according to the present invention had a superior activity than that of the conventionally modified papain.

Experimental Example 4

GE-1 and GE-3 in Preparation Examples 1 or 3, respectively were measured for their safety to the skin in terms of skin irritation by comparing those of the native papain having the same enzyme titer.

The skin irritation was determined by measuring redness caused by the enzyme application. Thus, the enzyme solution (20 $\mu$l) was applied to the skin twice a day for consecutive 7 days, and the skin color was measured by using Chromameter CM2002 at days 0, 3, 5, and 7. The redness index was calculated with regard the value 100 for the day 0 (initial skin color). Thus obtained redness index has a statistical significance of <0.05 when tested by Anova test.

The results are shown in Table 4.

TABLE 4

(Unit: Redness Index)

| | Control (Distilled water) | Prep. Ex. 1 (GE-1) | | Prep. Ex. 3 (GE-3) | | Native Papain | |
|---|---|---|---|---|---|---|---|
| | | Stock | 1/100 Dilution | Stock | 1/100 Dilution | Stock | 1/100 Dilution |
| Day 0 | 100.00 | 100.00 | 100.00 | 100.00 | 100.00 | 100.00 | 100.00 |
| Day 3 | 100.85 | 100.55 | 101.23 | 102.34 | 100.04 | 189.04 | 165.02 |
| Day 5 | 103.58 | 103.02 | 98.56 | 98.76 | 100.05 | 225.08 | 192.78 |
| Day 7 | 102.95 | 101.55 | 100.04 | 97.98 | 99.13 | 230.24 | 203.44 |

As can be seen from Table 4, the stock of the papain modified according to the present invention shows no skin irritation while even the 1/100 dilution of native papain showed skin irritation.

Experimental Example 5

The stability of glucan-hrEGF conjugate in Preparation Example 4 was compared with that of native human recombinant epidermal growth factor("hrEGF") by measuring their fibroblast growth activity.

Thus, human fibroblast grown in a Dulbecco's Modified Eagle's Media (DMEM) containing 2.5% of bovine fetal serum was distributed onto 96-well microtiter plate to 5,000 cells/well.

The glucan-hrEGF conjugate or native hrEGF was dissolved in distilled water to a same concentration and allowed to stand at 37° C. for 7 days ("Pretreatment"). The pretreated glucan-hrEGF conjugate, pretreated native hrEGF or fresh native hrEGF was added to the above microtiter plate and grown for additional four days. After the growth, 50 µl of 0.2% solution of MTT(3-[4,5-dimethylthiazo-2-yl]-2,5-diphenyltetrazolium bromide ) was added to each well and the cultivation was carried out at 37° C. for 4 hours. The formazan formed in the well was dissolved by adding DMSO(Dimethyl sulfoxide). The absorbance of formazan was measured at 570 nm with a microplate reader. By comparing the absorbance of the pretreated groups with that of the untreated group, the growth of fibroblast was evaluated. The results are shown in Table 5.

TABLE 5

Unit: % in cells survived

| Dilution | Fresh native hrEGF | Pretreated glucan-hrEGF conjugate | Pretreated native hrEGF |
|---|---|---|---|
| $10^{-2}$ | 121.0 | 128.2 | 88.7 |
| $10^{-3}$ | 126.8 | 128.9 | 94.9 |
| $10^{-4}$ | 124.5 | 125.4 | 102.5 |
| $10^{-5}$ | 112.9 | 112.8 | 101.8 |

As can be seen from Table 5, when comparing to the untreated native hrEGF, the glucan-hrEGF conjugate according to the invention retains its ability of cell growth even when it is pretreated to induce an activity loss while the native hrEGF loses the most of its activity. Therefore, it is affirmed that the protein modified according to the present invention has an improved stability.

These foregoing Examples prove that the protein coupled to glucan provided by the present invention retains its activity for a prolonged time, causes no skin irritation and shows a greater action on the insoluble substrates.

Experimental Example 6

Skin lotions (Formulation 1, and Comparative Formulations 1 and 2) having the composition shown in Table 6 were prepared and evaluated for their protein lysis activity by the same method in Experimental Example 1. The results are shown in Table 7.

TABLE 6

Unit: wt %

| Ingredients | Formulation 1 | Comparative Formulation 1 | Comparative Formulation 2 |
|---|---|---|---|
| Papain in Prep. Ex. 1 | 0.1 | — | — |
| Native Papain | — | 0.1 | — |
| Papain in Comp. Prep. Ex. 1 | — | — | 0.1 |
| Glycerin | 3.0 | 3.0 | 3.0 |
| Butylene Glycol | 2.0 | 2.0 | 2.0 |
| Propylene Glycol | 2.0 | 2.0 | 2.0 |
| Carboxyvinyl Polymer | 0.1 | 0.1 | 0.1 |
| PEG-12 Nonylphenyl Ether | 0.2 | 0.2 | 0.2 |
| Polysorbate 80 | 0.4 | 0.4 | 0.4 |
| Ethanol | 10.0 | 10.0 | 10.0 |
| Triethanolamine | 0.1 | 0.1 | 0.1 |
| Preservatives, Pigments, Perfumes | q.s. | q.s. | q.s. |
| Distilled water | To 100 | To 100 | To 100 |

TABLE 7

Unit: wt %

| | Formulation 1 | | Comp. Formulation 1 | | Comp. Formulation 2 | |
|---|---|---|---|---|---|---|
| | 30° C. | 45° C. | 30° C. | 45° C. | 30° C. | 45° C. |
| Day 0 | 100 | 100 | 100 | 100 | 100 | 100 |
| Day 10 | 100 | 100 | 20 | 11 | 45 | 20 |
| Day 30 | 100 | 100 | 5 | 0 | 12 | 10 |
| Day 60 | 100 | 100 | 0 | 0 | 4 | 0 |
| Day 90 | 100 | 97 | 0 | 0 | 0 | 0 |

The results in Table 7 prove that the enzyme modified according to the present invention shows the greatest stability within the composition.

Experimental Example 7

Skin lotions in Formulation 1, or Comparative Formulations 1 or 2 were evaluated for their action on corneum by the same method in Experimental Example 3. The results are shown in Table 8.

TABLE 8

Unit: Disintegration %

|  | Formulation 1 | Comp. Formulation 1 | Comp. Formulation 2 |
|---|---|---|---|
| Hour 0 | 100 | 100 | 100 |
| Hour 12 | 100 | 20 | 45 |
| Hour 24 | 100 | 5 | 12 |
| Hour 36 | 100 | 0 | 4 |
| Hour 48 | 100 | 0 | 0 |

The results in Table 8 prove that the enzyme modified according to the present invention shows the greatest action on the corneum disintegration.

Experimental Example 9

Skin lotions of Formulation 1 and Comparative Formulation 1 were evaluated for their safety on the skin. Thus, skin lotion (1 mg) was applied to the skin twice a day for consecutive 7 days, and the skin color was measured by using Chromameter CM2002 at days 0, 3, 5, and 7. The redness index was calculated with regard the value 100 for the day 0 (initial skin color). Thus obtained redness index has a statistical significance of <0.05 when tested by Anova test.

The results are shown in Table 9.

TABLE 9

(Unit: Redness Index)

|  | Control (Distilled water) | Formulation 1 | Comp. Formulation 1 |
|---|---|---|---|
| Day 0 | 100.00 | 100.00 | 100.00 |
| Day 3 | 100.85 | 100.55 | 191.00 |
| Day 5 | 107.51 | 100.02 | 225.05 |
| Day 7 | 102.85 | 101.51 | 238.42 |

As can be seen from Table 9, the skin lotion containing papain modified according to the present invention shows no skin irritation while the skin lotion containing the native papain showed a severe skin irritation.

Based on the results of the above Experimental Examples, the following various formulations are provided. These formulations can be applied to the skin to attain a certain effect rendered by the protein incorporated therein for a prolonged time without skin irritation. These formulations should not be construed to limit the scope of the invention.

Formulation Example 2

Nutrient Skin Lotion

| Ingredients | Wt % |
|---|---|
| GE2 in Preparation Example 2 | 0.1 |
| Squalane | 5.0 |
| Bee-wax | 4.0 |
| Polysorbate 60 | 1.5 |
| Sorbitan Cesquioleate | 1.5 |

-continued

| Ingredients | Wt % |
|---|---|
| Fluid paraffin | 0.5 |
| Carprylic/Capric triglyceride | 5.0 |
| Glycerin | 3.0 |
| Butylene glycol | 3.0 |
| Propylene glycol | 3.0 |
| Carboxyvinyl polymer | 0.1 |
| Triethanolamine | 0.2 |
| Preservatives, Pigments, perfumes | q.s. |
| Distilled water | To 100 |

Formulation Example 3

Nutrient Skin Cream

| Ingredients | Wt % |
|---|---|
| GE3 in Preparation Example 3 | 0.1 |
| Bee-wax | 10.0 |
| Polysorbate 60 | 1.5 |
| PEG-60 hardened castor oil | 2.0 |
| Sorbitan Cesquioleate | 0.5 |
| Fluid paraffin | 10.0 |
| Squalane | 5.0 |
| Carprylic/Capric triglyceride | 5.0 |
| Glycerin | 5.0 |
| Butylene glycol | 3.0 |
| Propylene glycol | 3.0 |
| Triethanolamine | 0.2 |
| Preservatives, Pigments, perfumes | q.s. |
| Distilled water | To 100 |

Formulation Example 4

Massage Cream

| Ingredients | Wt % |
|---|---|
| GE1 in Preparation Example 1 | 0.1 |
| Bee-wax | 10.0 |
| Polysorbate 60 | 1.5 |
| PEG-60 hardened castor oil | 2.0 |
| Sorbitan Cesquioleate | 0.8 |
| Fluid paraffin | 40.0 |
| Squalane | 5.0 |
| Carprylic/Capric triglyceride | 4.0 |
| Glycerin | 5.0 |
| Butylene glycol | 3.0 |
| Propylene glycol | 3.0 |
| Triethanolamine | 0.2 |
| Preservatives, Pigments, perfumes | q.s. |
| Distilled water | To 100 |

Formulation Example 5

Facial Pack

| Ingredients | Wt % |
|---|---|
| GE1 in Preparation Example 1 | 0.1 |
| Polyvinyl alcohol | 13.0 |
| Sodium carboxyemthyl cellulose | 0.2 |
| Glycerine | 5.0 |

-continued

| Ingredients | Wt % |
| --- | --- |
| Alantoin | 0.1 |
| Ethanol | 6.0 |
| PEG-12 Nonylphenyl ether | 0.3 |
| Polysorbate | 0.3 |
| Preservatives, Pigments, perfumes | q.s. |
| Distilled water | To 100 |

Formulation Example 6

Facial Gel

| Ingredients | Wt % |
| --- | --- |
| GE2 in Preparation Example 2 | 0.1 |
| Sodium ethylene diamine acetate | 0.05 |
| Carboxy vinyl polymer | 0.3 |
| Ethanol | 5.0 |
| PEG-60 hardened castor oil | 0.5 |
| Triethanolamine | 0.3 |
| Preservatives, Pigments, perfumes | q.s. |
| Distilled water | To 100 |

Formulation Example 7

Ointment

| Ingredients | Wt % |
| --- | --- |
| Product in Preparation Example 4 | 0.1 |
| Bee-wax | 10.0 |
| Polysorbate 60 | 5.0 |
| PEG-60 hardened castor oil | 2.0 |
| Sorbitan Cesquioleate | 0.5 |
| Vaseline | 5.0 |
| Fluid paraffin | 10.0 |
| Squalane | 5.0 |
| Shea butter | 3.0 |
| Carprylic/Capric triglyceride | 5.0 |
| Glycerin | 10.0 |
| Propylene glycol | 10.2 |
| Triethanolamine | 0.2 |
| Preservatives, Pigments, perfumes | q.s. |
| Distilled water | To 100 |

Formulation Example 8

Gel-type Ointment (Topical Application)

| Ingredients | Wt % |
| --- | --- |
| Product in Preparation Example 4 | 3.0 |
| Polyacrylic acid (Carbopol 940) | 1.5 |
| Isopropanol | 5.0 |
| Hexylene glycol | 25.0 |
| Triethanolamine | 1.7 |
| Deionized water | To 100 |

Formulation Example 9

Patch (Topical Application)

| Ingredients | Wt % |
| --- | --- |
| Product in Preparation Example 4 | 3.0 |
| Hexylene glycol | 20.0 |
| Diethylamine | 0.7 |
| Polyacrylic acid (Carbopol 934P) | 1.0 |
| Sodium sulfite | 0.1 |
| Polyoxyethylene lauryl ether (E.0. = 9) | 1.0 |
| Polyhydroxyethylene cetyl stearyl ether (Cetomacrogol 1000) | 1.0 |
| Viscous paraffin oil | 2.5 |
| Caprylic ester/Capric ester (Cetiol LC) | 2.5 |
| Polyethylene glycol 400 | 3.0 |
| Deionized water | To 100 |

Although preferred embodiments of the present invention have been described in detail hereinabove, it should be clearly understood that many variations and/or modifications of the basic inventive concepts herein taught which may appear to those skilled in the art will still fall within the spirit and scope of the present invention as defined in the appended claims.

What is claimed is:

1. A protein modified to improve its stability, said modified protein being coupled to a β-1,3-glucan branched with β-1,6-linkage, wherein said β-1,3-glucan comprises one β-1,6-linkage for every three β-1,3-main chains.

2. The modified protein of claim 1, wherein said β-1,3-glucan branched with β-1,6-linkage is schizophyllan or scleroglucan.

3. The modified protein of claim 1, wherein said protein is selected from the group consisting of papain, bromelain, ficin, trypsin, chymotrypsin, collagenase, elastase, plasmin, bacterial protease, α-amylase, glucoamylase, cellulase, pectinase, xylanase, α-glucosidase, β-glucosidase, α-galactosidase, β-galactosidase, β-glucanase, chitinase, mannanase, phospholipase, triacylglycerol hydrolase, DNase, RNase, phosphatases, lysozymes, catalases, super-oxide dismutases, transglutamninases, peroxidases, photolyases, cytokines, growth factors, hormones, immunoglobulins, lactoferrins, metallothioneins and thioredoxins.

4. A method for modifying protein to improve its stability which comprises the step of coupling the protein to a β-1,3-glucan branched with β-1,6-linkage, wherein said β-1,3-glucan comprises one β-1,6-linkage for every three β-1,3-main chains.

5. A method of claim 4, wherein the coupling comprises the steps of
   (a) reacting said glucan with periodates to oxidize β-1,6-residues of the glucan to form aldehydes;
   (b) removing unreacted periodates from the reaction solution;
   (c) adding to the reaction solution a protein in an amount of 0.00001~10.0% by weight and allowing the protein to react with the oxidized glucan; and
   (d) adding to the reaction solution a reducing agent in an amount of 0.0001~1.0% by weight.

6. A method of claim 5, which further comprises the step of (e) washing the product in the step (d).

7. A method of claim 5, wherein, when two or more proteins are modified a first protein is added to the reaction mixture in the step (c) and proteins are added to the reaction mixture in the step (d), wherein not all of the aldehydes formed in step (a) react with the first protein in step (c).

8. A method of claim 4, wherein said protein is selected from the group consisting of papain, bromelain, ficin, trypsin, chymotrypsin, collagenase, elastase, plasmin, bacterial protease, α-amylase, glucoamylase, cellulase, pectinase, xylanase, α-glucosidase, β-glucosidase, α-galactosidase, β-galactosidase, β-glucanase, chitinase, mannanase, phospholipase, triacylglycerol hydrolase, DNase, RNase, phosphatases, lysozymes, catalases, superoxide dismutases, transglutamninases, peroxidases, photolyases, cytokines, growth factors, hormones, immunoglobulins, lactoferrins, metallothioneins and thioredoxins.

9. A method of claim 4, wherein said β-1,3-glucan branched with β-1,6 linkage is schizophyllan or scleroglucan.

10. A method of claim 9 wherein said β-1,3-glucan branched with β-1,6-linkage is one of those subjected to the molecular weight adjustment using a microfluidizer, sonicator or β-1,3-glucanase.

11. A composition for external or topical application which comprises the modified protein of claim 1 in an amount of 0.00001~100% by weight based on the total weight of the composition and a dermatologically or cosmetically acceptable vehicle.

12. A composition of claim 11, which is a cosmetic composition selected from the group consisting of cleansing lotion, cleansing cream, skin milk, emollient lotion, massage cream, emollient cream, make-up base, lipstick, facial pack, facial gel, shampoos, rinses, hair-tonics and soaps.

13. A composition of claim 11, which is a dermatological composition selected from the group consisting of lotions, ointments, gels, creams, patches and sprays.

* * * * *